(12) United States Patent
Pelsue et al.

(10) Patent No.: US 6,633,338 B1
(45) Date of Patent: Oct. 14, 2003

(54) PROGRAMMABLE ILLUMINATOR FOR VISION SYSTEM

(75) Inventors: Kurt Pelsue, Wayland, MA (US); Jonathan S. Ehrmann, Sudbury, MA (US)

(73) Assignee: GSI Lumonics, Inc., Kanata (CA)

( * ) Notice: Subject to any disclaimer, the term of this patent is extended or adjusted under 35 U.S.C. 154(b) by 0 days.

(21) Appl. No.: 09/301,002

(22) Filed: Apr. 27, 1999

(51) Int. Cl.[7] .......................... H04N 5/222; H04N 7/00
(52) U.S. Cl. .................................... 348/370; 348/31
(58) Field of Search ........................ 348/67, 68, 69, 348/70, 195, 203, 205, 370, 86, 87, 88, 31, 131

(56) References Cited

U.S. PATENT DOCUMENTS

| | | | |
|---|---|---|---|
| 4,475,796 A | 10/1984 | Kimura | 350/525 |
| 4,484,069 A | 11/1984 | Brenholdt | 250/201 |
| 4,604,648 A * | 8/1986 | Kley | 348/131 |
| 4,706,168 A | 11/1987 | Weisner | 362/18 |
| 4,893,223 A | 1/1990 | Arnold | 362/252 |
| 4,918,284 A | 4/1990 | Weisz | 219/121.78 |
| 4,972,093 A | 11/1990 | Cochran et al. | 250/572 |
| 5,038,258 A | 8/1991 | Koch et al. | 362/237 |
| 5,185,638 A | 2/1993 | Conzola et al. | 356/237 |
| 5,515,452 A * | 5/1996 | Penkethman et al. | 382/141 |
| 5,519,496 A | 5/1996 | Borgert et al. | 356/394 |
| 5,585,616 A * | 12/1996 | Roxby et al. | 235/462.06 |
| 5,615,013 A * | 3/1997 | Rueb et al. | 356/394 |
| 5,684,530 A * | 11/1997 | White | 348/131 |
| 5,724,139 A * | 3/1998 | Guerra | 356/600 |
| 5,737,122 A | 4/1998 | Wilt et al. | 359/436 |
| 5,822,053 A | 10/1998 | Thrailkill | 356/237 |

* cited by examiner

Primary Examiner—Wendy R. Garber
Assistant Examiner—Luong Nguyen
(74) Attorney, Agent, or Firm—Cesari and McKenna, LLP

(57) ABSTRACT

The field portion (40) of a workpiece (14) that an electro-optical system (28) can image is deflected by a field-of-view deflector (38) and an array of light sources (42, 44) illuminates the workpiece. As the field of view (40) moves about the workpiece surface, individual sources (42, 44) in the light-source array are so turned on and off that all sources that could be imaged into the field of view by specular reflection are turned off. In this way, proper dark-field illumination is maintained.

18 Claims, 5 Drawing Sheets

PROGRAMMABLE ILLUMINATOR FOR VISION SYSTEM

BACKGROUND OF THE INVENTION

The present invention is directed to machine vision and in particular to providing illumination for such systems.

Machine vision has been applied to a number of production and testing tasks. In general, workpieces, such as printed-circuit boards, integrated-circuit chips, and other articles of manufacture are brought into the field of view of a camera. The camera typically generates an image in digital form, which digital circuitry normally in the form of a microprocessor and related circuitry processes in accordance with the task to be performed.

In many cases, the workpiece is too large for a practical-sized camera to image with adequate resolution, but this problem is readily solved by taking an image of only a small part of the workpiece at any single time. This yields the requisite resolution, and is images of respective segments of the workpiece can be taken as the workpiece is stepped through the camera's field of view.

Although this approach is acceptable in a number of applications, it can be throughput- and accuracy-limiting in some others. There are often practical limits to the speed at which the workpiece can be advanced through the camera's field of view. Additionally, the need for accurate correlation between successive images can impose severe accuracy requirements on the workpiece-advancing system. To a greater or lesser degree, the same limitations apply regardless of whether it is the camera or the workpiece that is moved.

For some applications, a superior solution is to move neither the camera nor the workpiece, but rather to move the camera's field of view by employing deflector mechanisms. Galvanometer-mounted pivoting mirrors, pivoting prisms, and rotating reflector polygons are among the mechanisms commonly employed in optical systems to perform image deflection. Although these still are moving parts, they are ordinarily relatively small and take advantage of optical leverage to change the field of view faster than systems that move the entire workpiece or camera.

Despite this advantage, there is a class of applications to which workers in this field have been slow to apply the field-of-view-deflection approach. One example of this class is the type of application that involves reading laser-scribed marks on workpieces such as semiconductor wafers or electronic-component packages. Marks of that type are hard to detect reliably because they are quite subtle. So considerable effort has been applied to illuminating the workpiece in such a manner as to minimize noise contributed by surface irregularities in non-marked regions. But achieving this result is greatly complicated in systems that use field-of-view deflectors. In systems that move the workpiece or the camera, the illumination apparatus always has the same position with respect to the field of view, so illumination characteristics need to be optimized for that relationship only. In field-of-view-deflector systems, on the other hand, the lighting system would have to be optimized for a wide range of resultant relationships between the lighting system's position and that of the camera's field of view. For some applications, the difficulty of solving this problem has confounded attempts to employ field-of-view deflection.

SUMMARY OF THE INVENTION

But we have recognized that imaging results for such systems can be greatly improved by emphasizing the dark-field-illumination aspects of the problem and adapting to it a method previously used to vary dark-field illumination in response to camera-objective changes.

"Dark-field illumination" is an illumination approach that takes advantage of the fact that a specularly reflecting feature in the midst of a diffuse-reflecting background will appear dark if that feature's specular reflection images the main light source outside the camera's field of view. That is, since the angle of reflection of all light striking a specular reflector equals that light's angle of incidence, the reflected light will not pass through the camera's entrance pupil unless that sole angle of reflection yields that result. But light striking the diffusely reflecting background is reflected in a range of angles, so a substantial amount may enter the camera even if the specular-reflection angle would not result in a ray that does. The specularly reflecting feature is therefore readily identified because it appears dark against a lighter background.

Because of this effect, there is a rich store of work directed to dark-field illumination, and we have recognized that properly adapting it can yield significantly improved results for field-of-view-deflection systems. It had long ago been recognized in systems such as that described in U.S. Pat. No. 4,604,648 to Kley that individual elements of a light-source array should be selectively operated in accordance with the particular objective or zoom position of the imaging camera. We have adapted this concept by so operating elements of a light-source array that the position within the array at which one or more light sources is not lit moves around the array as the deflector changes the field of view's position.

Specifically, as the deflector so moves as to change the field of view on the workpiece, we selectively turn off any elements of the source array that will be imaged into the camera's field if specular reflection occurs in the portion of the workpiece within that field of view. As the field of view moves so that an element previously thus imaged no longer is, the element is typically turned on again.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
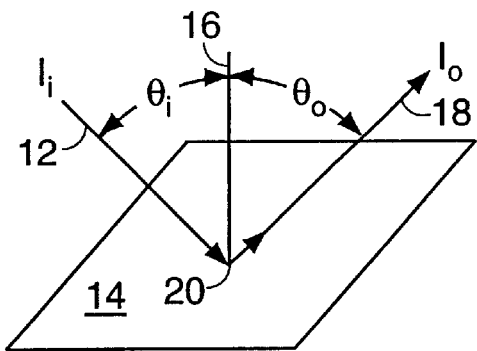
FIG. 1 is a diagram that illustrates specular reflection.

Before we describe the system of the present invention, we briefly review the concept of dark-field illumination. In FIG. 1, an incident ray 12 strikes a specularly reflecting surface 14 at an angle $\theta_i$ with respect to the normal 16 to that surface. If the surface 14 is a mirror or other specularly reflecting surface, essentially all light that strikes the surface at the angle of incidence $\theta_i$ reflects at an angle of reflection $\theta_o$ equal to the angle of incidence $\theta_i$. The point 20 at which the light ray strikes the surface 14 may be located within the field of view of a camera, but that light will not contribute to the camera image unless ray 18 extends through that camera's entrance pupil. For the purposes of this discussion, we will assume that it does not. So point 20 is not illuminated so far as the camera is concerned.

Figure 2:
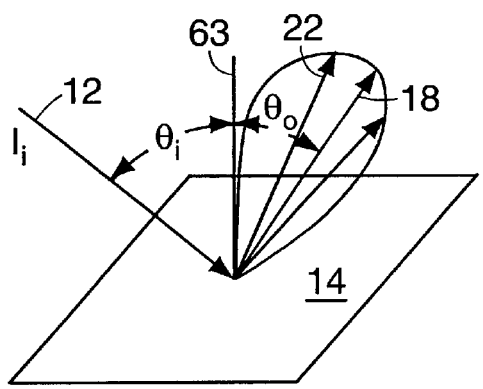
FIG. 2 is a similar diagram that illustrates diffuse reflection.

Now consider FIG. 2, where we change the specular-reflection assumption and instead assume that the target surface 14 is a diffuse reflector. In that case, the reflection of ray 12 includes not only ray 18, whose angle of reflection equals the angle of incidence, but also a plume of other rays, such as ray 22, whose angles with the normal differ from that of the incident ray. The camera pupil may be so positioned that it receives some of these rays even if it does not receive ray 18. So spot 20 is illuminated from the camera's point of view, even though it would not be if it reflected only specularly.

Figure 3:
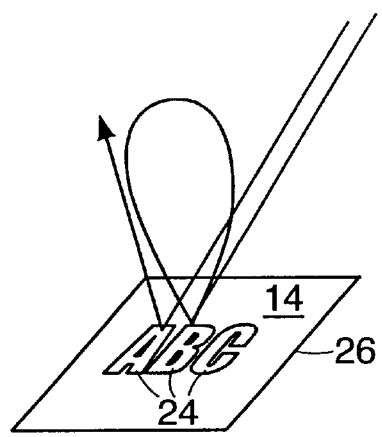
FIG. 3 is a diagram that illustrates specularly reflecting indicia in a diffusely reflecting background.

If the surface 14 includes both FIG. 3's specularly reflecting indicia 24 and its diffuse background 26, an image is formed in which the indicia are readily distinguished if the camera is positioned with an entrance pupil that does not receive the specularly reflected rays but does receive some of the rays that result from diffuse reflection. Of course, the indicia may not have perfectly mirror-like surfaces, as the drawing suggests, but they will be distinguishable so long as they yield light plumes that are significantly more compact than the plumes produces by the indicia's surroundings.

Figure 4:
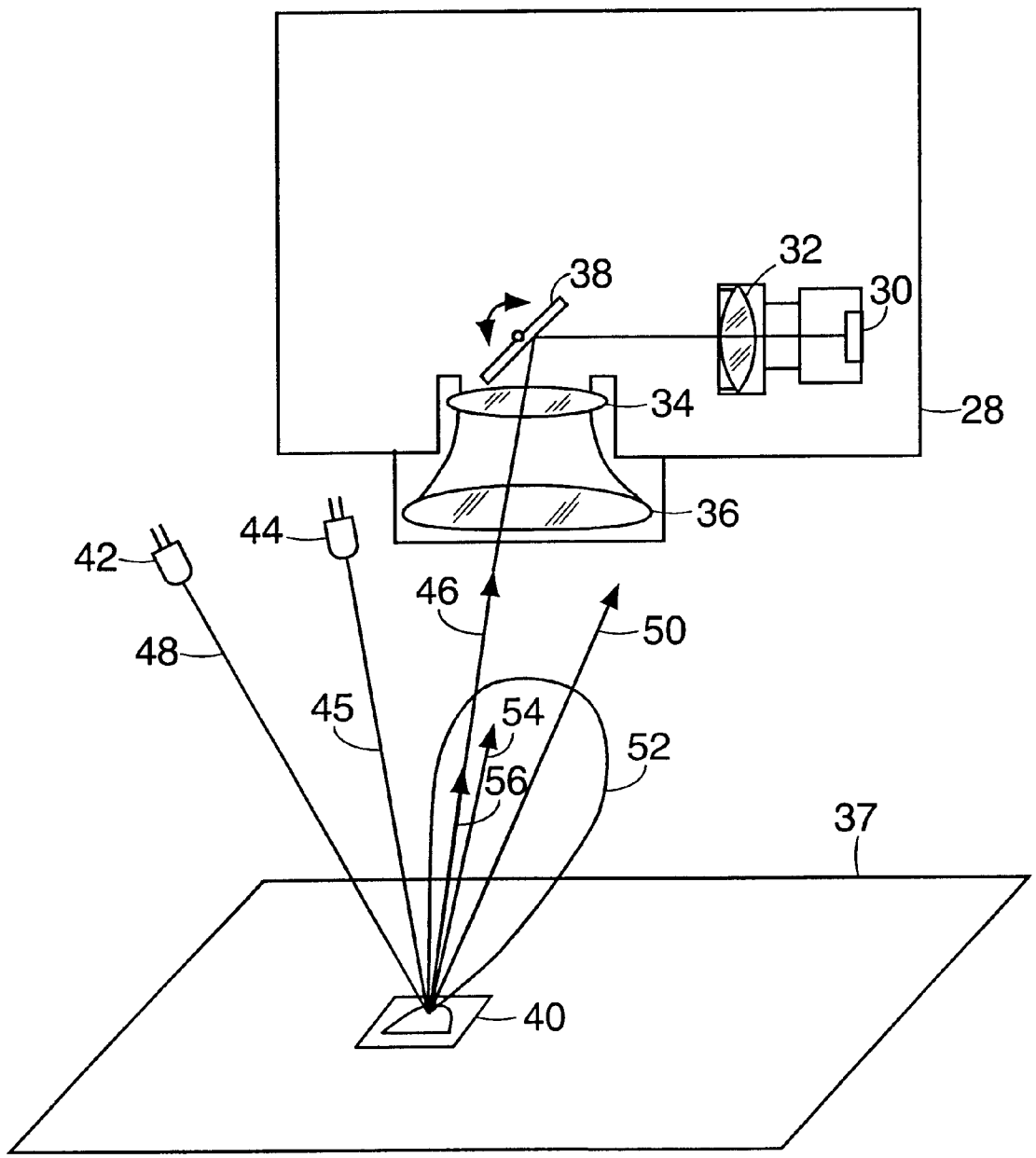
FIG. 4 is a diagram of a vision system that employs the present invention's teachings.

FIG. 4 depicts an apparatus for applying the technique of dark-field illumination to a field-of-view-deflection system. In an electro-optical process head 28 is mounted a camera that includes a detector 30, lenses 32, 34, and 36, and a field-of-view deflector depicted for purposes of illustration as including a galvanometer-mounted mirror 38. Detector 30 will typically take the form of an array of charge-coupled devices, whose outputs are converted to digital form for processing in accordance with the particular application to which the system is applied.

Other detection devices can be employed, of course, as can lens systems different from that of FIG. 4. That lens system includes an image-forming lens 32 spaced by its focal length from the detector 30. It also includes collimating lenses 34 and 36, which collimate the light from a target region in which a workpiece 37 is disposed; i.e., lenses 34 and 36 image workpiece 37 at infinity. But other embodiments may, say, include only a single lens, corresponding to lens 32 but positioned to image the workpiece 37 on the detector 30.

Extending downward to infinity from the electro-optical head 28 is a camera field of view consisting of a volume of points in space from which the lenses and field-of-view deflector provide optical paths to the detector 30. The field of view intersects the target region so that the camera can "see" a portion 40 of the workpiece. The field-of-view deflector's position determines where on the workpiece portion 40 falls; i.e., the field viewed by the detector can change without relative movement between the camera and the workpiece, although such movement may occur, too. For instance, the workpiece may be on a conveyor, which typically would not be capable of moving as quickly as the field of view.

Although the drawing depicts the field-of-view deflector as comprising only a single mirror, many embodiments of the present invention will employ two, which deflect the camera's field of view along mutually orthogonal axes. Also, although the drawing shows lenses 34 and 36 between the mirror 38 and the workpiece 37, some embodiments that employ collimating lenses may instead place them between the field-of-view deflector and the detector.

To illuminate the workpiece 37 so that the camera can form an adequate image, the system further includes an array of lamps suspended above the workpiece. For most of the present invention's embodiments, the number of such lamps will be relatively large, but FIG. 4 depicts only two such lamps, 42 and 44, which are controlled by illumination-control circuitry not shown in FIG. 4. Operation of these lamps is coordinated with the position of the mirror 38 and thus of the camera's field of view. As that mirror pivots, the workpiece portion 40 of which the camera can form an image on the detector 30 moves about the workpiece's surface.

In accordance with the present invention, most or a significant portion of the lamps in the array shine on the workpiece at any given time, but selected ones are prevented from doing so as the portion 40 within the field of view moves about the surface of the workpiece 37. As that portion 40 moves, any lamp is prevented from shining on the workpiece if under the assumption of specular reflection it would be imaged into the field of view. That is, any source that the camera could "see" if the workpiece portion 40 were a mirror is prevented from shining on the workpiece so that the camera receives no specular reflection from it. As the mirror 38 continues moving and continues to deflect the camera's field of view, lamps prevented from shining on the workpiece to prevent specular reflection into the camera typically shine on it again after the field of view moves beyond their images. So a dark region of unlit sources moves about against a background of sources that are lit as the scanning process proceeds.

Any way of achieving such a dark region moving about a background of sources can be used. The "sources" can be reflectors, for instance, and "lit" array elements could be the reflectors on which a remote source or sources selectively shine, while the unlit elements would be the reflectors on which the source or sources do not shine. Another approach is to provide continuously operating lamps and selectively operable baffles that can selectively hide lamps from the workpiece; the "lit" elements would be the lamps not hidden. Preferably, though, the array elements consist of respective light-emitting diodes ("LEDs") that are simply turned on to cause them to shine on the workpiece and turned off to prevent them from doing so, and the following description is based on this assumption.

To determine which lamps are in the "viewed" subset and should thus be turned off, we assume that the workpiece is a mirror. Under this assumption, an example ray 45 emitted by source 44 will be reflected along path 46 to contribute to formation of the image on detector 30. That is, if region 40 were a mirror, at least part of source 44 would be Is imaged into the camera's field of view. Any source for which this is true is part of the viewed subset and is therefore turned off. Source 42, on the other hand, remains lit because specular reflection of any rays, such as ray 48, that strike region 40 will result in rays, such as ray 50, that do not enter the camera: that source belongs in the "unviewed" set. (We note in passing that the "mirror" 40 need not have the horizontal orientation that the drawing depicts; any expected workpiece-surface angle can be used for determining the viewed and unviewed sets' respective memberships.) Source 42 contributes to the image because any diffuse reflection resulting from ray 48 will result in a plume of rays 52, of which some, such as rays 54 and 56, pass through the camera's entrance pupil.

As deflection continues, the portion 40 viewable by the camera 28 may reach a point from which specular reflection in response to light from source 42 would produce rays that contribute to the image on detector 30 whereas reflection of light from source 44 would no longer do so. When the deflector reaches such a point, source 42 will be turned off and source 44 will typically be turned back on. Note that this operation of turning off selected elements occurs in addition to other illumination-control operations that may be occurring. It may be desirable, for instance, to operate different ones of the sources with differing intensities so as to achieve illumination that is optimally uniform for the currently prevailing camera angle. Also, the sources that "remain" lit may actually be strobed so as to "freeze" the workpiece image despite continuous relative motion between the camera's field of view and the workpiece.

Controlling the sources can take any of a number of forms. Since it is well within the skill of those familiar with such optical systems to predict which sources can be "seen" at various angles, an algorithm for converting scan-angle position to lamp selection can readily be written, and the determination can accordingly be made algorithmically in real time. Or that calculation can be made ahead of time to populate a look-up table used to make the real-time conversion from field-of-view position to lamp selection. Alternatively, the look-up table could be populated in accordance with experimental results. Regardless of how the look-up table is populated, it can be used in a straight table look-up or as part of a combination of table look-up, and, say real-time interpolation.

Figure 5:
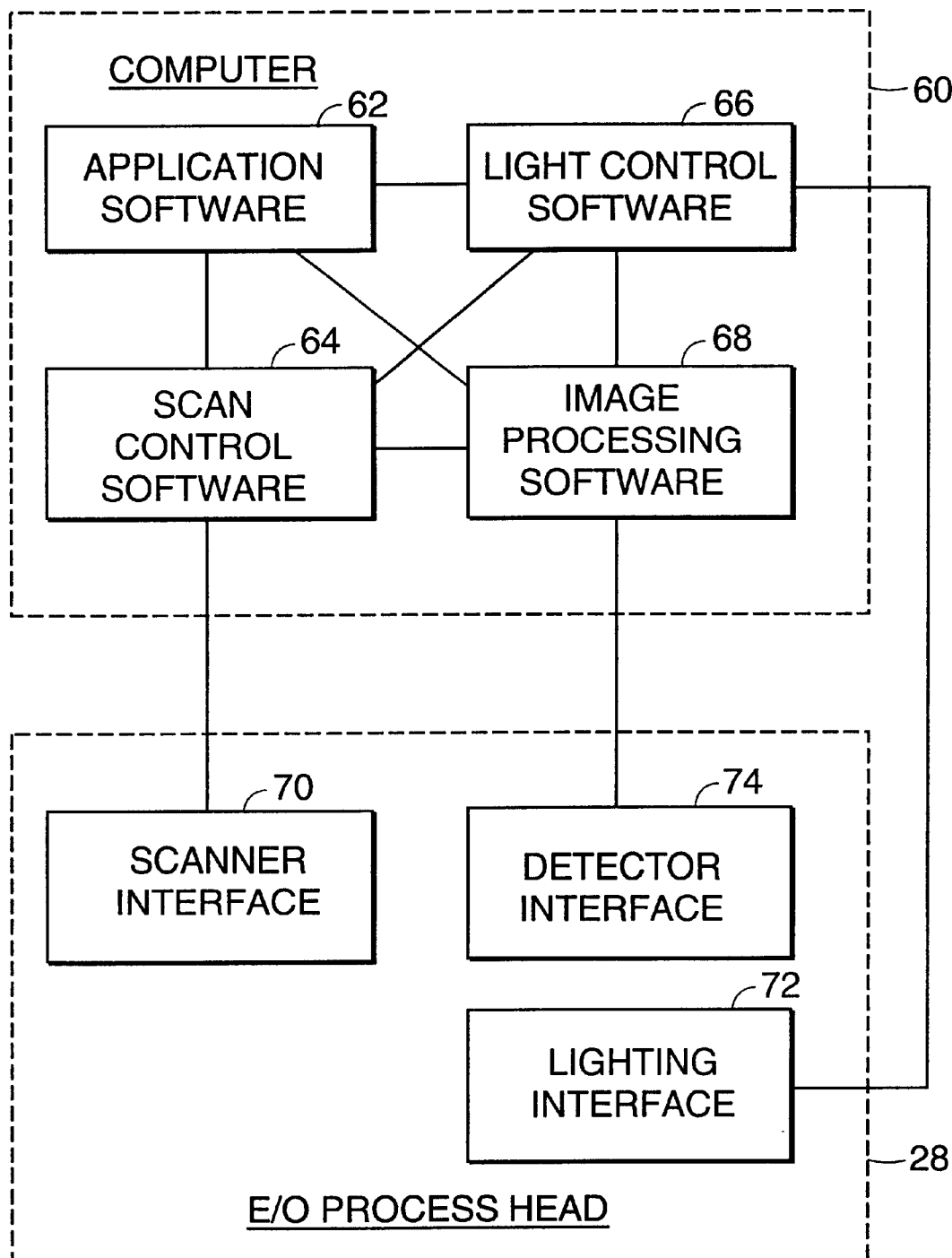
FIG. 5 is a block diagram of the control system that an application using the FIG. 4 system may employ.
Figure 6:
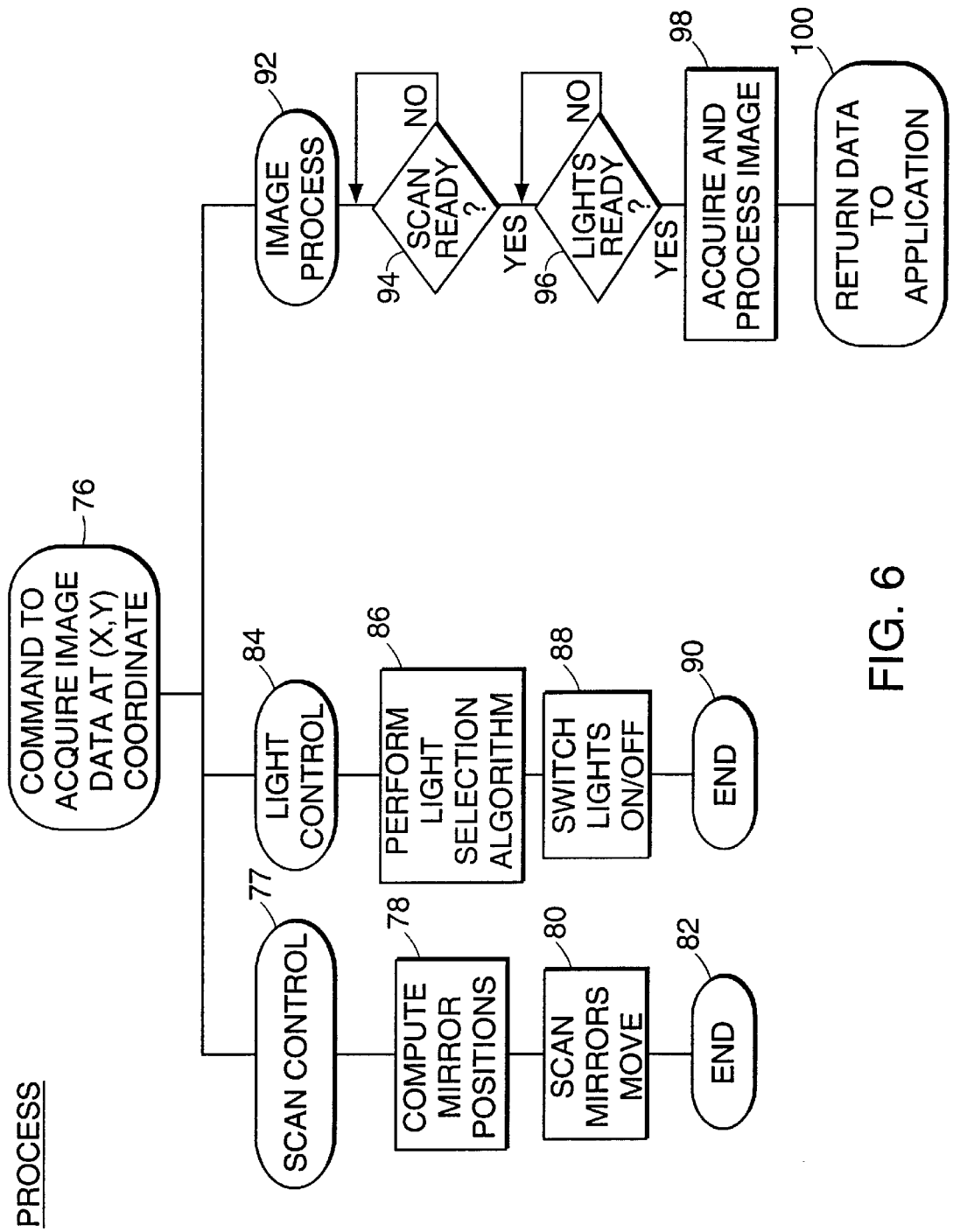
FIG. 6 is a diagram of the processes that the system of FIG. 5 performs.

FIGS. 5 and 6 show how machine-vision applications will typically implement the present invention's teachings. Although it is apparent that dedicated "random logic" could be separately designed for each of the functions to be described below, most embodiments will employ programming to configure common microprocessor circuitry to act as the various circuits for performing these operations. So FIG. 6 depicts the systems as including a computer 60 that runs a software application 62 for which image data are required. To this end, the application may operate various other software modules such as modules 64, 66, and 68, which respectively control the field-of-view deflector, lights, and detector. Under direction from these modules, the computer 60 communicates with appropriate interface circuitry represented by blocks 70, 72, and 74 to coordinate these operations.

As FIG. 6 indicates, an application requiring image data would perform a routine whose object is to acquire image data at a particular location. FIG. 6's block 76 represents entering such a routine. This routine may concurrently call FIG. 5's several processes 64, 66, and 68. As FIG. 6 indicates, the scan-control whose entry block 77 represents would typically perform operations such as computing the deflector positions required to place the field of view in the desired location. Block 78 represents this step. Once the appropriate locations are determined, the scan-control process would cause FIG. 5's scanner interface to move, say, a galvanometer to produce the desired field-of-view deflection. Block 80 represents this operation, after which the process terminates in a step 82. That step may include setting a flag to indicate that the movement operation has been completed.

FIG. 6's block 84 represents entering the light-control process, which includes determining from the commanded field-of-view location which lamps' need to be switched on or off. Block 86 represents performing this conversion, which, as was explained above, may involve an algorithmic determination, a table look-up, or a combination of both. Once the desired light actuations are determined, they are performed by communications with FIG. 5's lighting interface 72 in a step that FIG. 6's block 88 represents. That drawing's block 90 represents ending the process in a step that may involve setting a flag to indicate that the lights have been properly set.

The image-processing operation, whose entry FIG. 6's block 92 represents, depends on proper illumination and proper positioning of the field-of-view deflector. Block 94 accordingly represents testing the scan-control operation's flag to determine whether the field of view is positioned as required. Once it has determined that the desired position has been reached, the process proceeds to step 96 to determine whether the illumination has been set properly. If it has, the process operates FIG. 5's detector interface 74 to obtain the camera's output data, as block 98 indicates, and the resultant data are supplied to the requesting application, as block 100 indicates.

Figure 7:
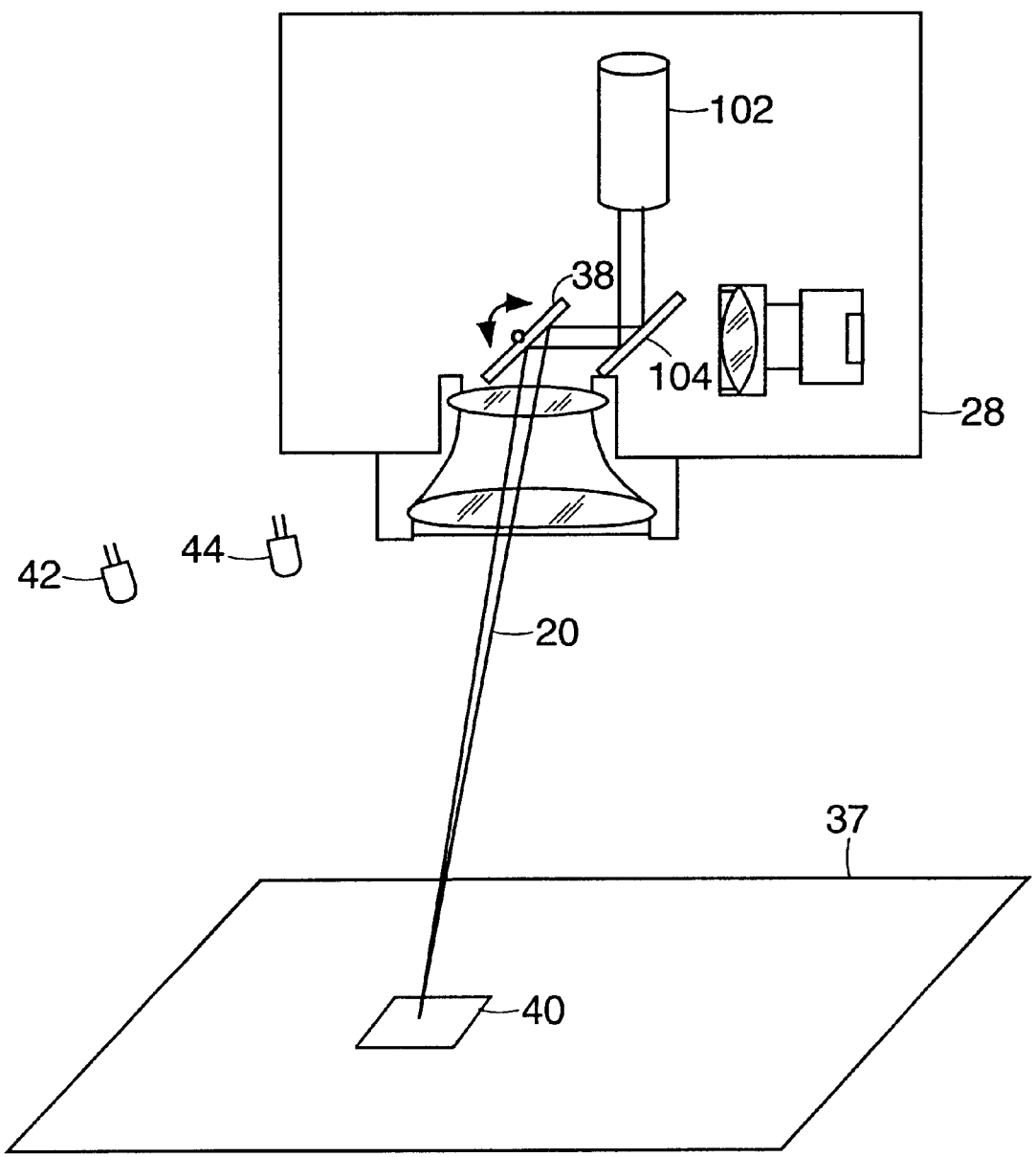
FIG. 7 is a diagram of the system that employs the present invention's teachings in a laser-scribing system.

The particular nature of whatever application 62 the invention supports is not a feature of the invention, but FIG. 7 illustrates one example of an apparatus in which the present invention is advantageous. The apparatus in FIG. 7 differs from that of FIG. 4 in that it additionally includes a laser source 102 and a beam splitter 104. And, in addition to the program modules depicted in FIG. 5, a system of the FIG. 7 type typically will include a module for controlling the laser as well as a laser interface by which that module exercises such control. To mark the workpiece, the beam splitter 104 cooperates with the field-of-view deflector 38 to direct the laser light to a workpiece location in the camera's field of view.

The application program may employ the vision system to identify fiducial marks or other identifying features previously made on the workpiece and thereby properly locate the position at which the new mark is to be made. The vision system also may be used to perform quality control on the marking process, possibly in a closed-loop fashion so as to adjust laser-beam positioning in accordance with the results of previous observations.

The system of FIG. 7 is more convenient than some prior-art marking systems. In such prior-art systems the marking apparatus was located separate from the imaging systems, in which there could be relative movement between the workpiece and the camera and lighting systems. In contrast, the illustrated system employs the same lens and deflector apparatus as the imaging system, so positions being inspected and marked are readily correlated.

It is another aspect of the present invention to reverse the arrangement described above in order to provide "bright field" illumination. This type of illumination is valuable when the background for the relatively specular indicia is relatively unreflective. In such a situation, it is preferable to emphasize reflection from the relatively specular indicia without unnecessarily illuminating the background. For this purpose, the sources that specular reflection would make visible at the source are the lit ones, and the others are the ones that are not lit.

From the foregoing description, it is apparent that the present invention can be employed in a wide range of embodiments and constitutes a significant advance in the art.

What is claimed is:

1. A machine-vision system comprising:
   A) a camera that has a field of view, includes a field-of-view deflector that moves the camera's field of view through positions in which it includes different portions of a target region, and is operable to sense an image of the field of view and generate output signals representative of the sensed image;
B) an array of light sources of which each is operable between a lit state, in which that light source shines light into the target region, and an unlit state, in which that light source does not, the light sources being so positioned that:
   i) if a target surface disposed at an expected target-surface angle in the portion of the target region included in the field of view reflects specularly, the target surface images a viewed subset of the sources into the camera's field of view and images an unviewed subset thereof outside the camera's field of view; and
   ii) the memberships of the viewed and unviewed subsets change with changes in the position of the camera's field of view; and
C) light-control circuitry that, when the camera takes an image, keeps each light source the viewed subset in the unlit state of that light source and permits each light source on the unviewed subset to assume the lit state of that light source.

2. A machine-vision system as defined in claim 1 wherein:
A) the camera includes a detector that generates the output signals representative of the image; and
B) the field-of-view deflector includes a galvanometer-mounted mirror that reflects light from the target surface toward the detector.

3. A machine-vision system as defined in claim 1 wherein the light-control circuitry determines the membership of the viewed subset algorithmically.

4. A machine-vision system as defined in claim 1 wherein the light-control circuitry employs a look-up table to determine the membership of the viewed subset.

5. A machine-vision system as defined in claim 4 wherein the light-control circuitry determines the membership of the viewed subset algorithmically.

6. A machine-vision system as defined in claim 1 further including a target-marking laser operable to emit laser light directed by the field-of-view deflector toward the target surface.

7. A machine-vision system comprising:
A) a camera that has a field of view, includes a field-of-view deflector that moves the camera's field of view through positions in which the camera's field of view includes different portions of a target region, and is operable to take an image of the field of view and generate output signals representative of the image;
B) a lighting system operable to illuminate a target surface selectively from a range of lighting positions such that:
   i) if the target surface is disposed at an expected target-surface angle in the portion of the target region included in the field of view and reflects specularly therefrom, the target surface images a viewed subset of the positions into the camera's field of view and images an unviewed subset thereof outside the camera's field of view; and
   ii) the memberships of the viewed and unviewed subsets change with changes in the position of the camera's field of view; and
C) light-control circuitry that, when the camera takes an image, operates the lighting system to prevent the lighting system from illuminating from the viewed subset the portion of the target region included in the field of view and permit the lighting system to illuminate from the unviewed subset the portion of the target region included in the field of view.

8. For taking images of a target, a method comprising:
A) providing a camera that has a field of view, includes a field-of-view deflector that moves the camera's field of view through positions in which the camera's field of view includes different portions of a target region, and is operable to take an image of the field of view and generate output signals representative of the image;
B) providing in the target region a target that forms a target surface;
C) providing an array of light sources of which each is operable between a lit state, in which that light source shines light on the target surface, and an unlit state, in which that light source does not, the light sources being so positioned that if the target suface reflects specularly, the target surface images a viewed subset of the sources into the camera's field of view and images an unviewed subset thereof outside the camera's field of view;
D) employing the field-of-view deflector to move the camera's field of view from a first position, in which at least a first said light source is a member of the viewed subset and at least a second said light source is a member of the unviewed subset, to a second position, in which at least the first light source is a member of the unviewed subset and at least the second light source is a member of the viewed subset;
E) while the field of view is in the first position:
   i) operating the camera to take an image of field of view; and
   ii) while doing so, keeping each light source of the viewed subset in the light source's unlit state but causing the second light source to assume the second light source lit state; and
F) while the field of view is in the second position:
   i) operating the camera to take an image of the field of view, and
   ii) while doing so, keeping each light source of the viewed subset in that light source's unlit state but causing the first light source to assume the first light source lit state.

9. A method as defined in claim 8 wherein:
A) the camera includes a detector that generates the output signals representative of the image; and
B) the field-of-view deflector includes a galvanometer-mounted mirror that reflects light from the target surface toward the detector.

10. A method as defined in claim 8 further including the step of determining the membership of the viewed subset algorithmically.

11. A method as defined in claim 8 further including the step of employing a look-up table to determine the membership of the viewed subset.

12. A method as defined in claim 11 further including the step of determining the membership of the viewed subset algorithmically.

13. A method as defined in claim 8 further including the step of operating a target-marketing laser to emit laser light directed by the field-of-view deflector toward the target surface.

14. For taking images of a target, a method comprising:
A) providing a camera that has a field of view, includes a field-of-view deflector that moves the camera's field of view through positions in which the camera's field of view includes different portions of a target region, and is operable to take an image of the field of view and generate output signals representative of the image;

B) providing a target that forms a target surface;
C) providing a lighting system operable to illuminate the target surface selectively from a range of lighting positions such that:
   i) if the target surface reflects specularly, the target surface images a viewed subset of the lighting positions into the camera's field of view and images an unviewed subset thereof outside the camera's field of view; and
   ii) the memberships of the viewed and unviewed subsets change with changes in the position of the camera's field of view;
D) employing the field-of-view deflector to move the camera's field of view from a first deflector position, in which at least a first said lighting position is a member of the viewed subset and at least a second said lighting position is a member of the unviewed subset, to a second deflector position, in which at least the first lighting position is a member of the unviewed subset and at least the second lighting position is a member of the viewed subset;
E) while the field of view is in the first deflector position:
   i) operating the camera to take an image of field of view; and
   ii) while doing so, preventing the lighting system from illuminating the target surface from the viewed subset but causing the lighting system to illuminate the target surface from the second lighting position; and
F) while the field of view is in the second deflector position:
   i) operating the camera to take an image of the field of view, and
   ii) while doing so, preventing the lighting system from illuminating the target surface from the viewed subset but causing the lighting system to illuminate the target surface from the first lighting position.

15. A machine-vision system comprising:
A) a camera that has a field of view, includes a field-of-view deflector that moves the camera's field of view through positions in which the camera's field of view includes different portions of a target region, and is operable to take an image of the field of view and generate output signals representative of the image;
B) an array of light sources of which each is operable between a lit state, in which that light source shines light into the target region, and an unlit state, in which that light source does not, the light sources being so positioned that:
   i) if a target surface disposed at an expected target-surface angle in the portion of the target region included in the field of view reflects specularly, the target surface images a viewed subset of the light sources into the camera's field of view and images an unviewed subset thereof outside the camera's field of view; and
   ii) the memberships of the viewed and unviewed subsets change with changes in the position of the camera's field of view; and
C) light-control circuitry that, when the camera takes an image, keeps each light source in the unviewed subset in that light source's unit state and permits each light source in the viewed subset to assume that light source's lit state.

16. A machine-vision system comprising:
A) a camera that has a field of view, includes a field-of-view deflector that moves the camera's field of view through positions in which the camera's field of view includes different portions of a target region, and is operable to take an image of the field of view and generate output signals representative of the image;
B) a lighting system operable to illuminate a target surface selectively from a range of lighting positions such that:
   i) if the target surface is disposed at an expected target-surface angle in the portion of the target region included in the field of view and reflects specularly therefrom, the target surface images a viewed subset of the positions into the camera's field of view and images an unviewed subset thereof outside the camera's field of view; and
   ii) the memberships of the viewed and unviewed subsets change with changes in the position of the camera's field of view; and
C) light-control circuitry that, when the camera takes an image, operates the lighting system to prevent the lighting system from illuminating the target region from the unviewed subset and permit the lighting system to illuminate the target region from the viewed subset.

17. For taking images of a target, a method comprising:
A) providing a camera that has a field of view and is operable to take an image of the field of view and generate output signals representative of the image;
B) providing a target that forms a target surface;
C) providing an array of light sources of which each is operable between a lit state, in which that light source shines light on the target, and an unlit state, in which that light source does not, the light sources being so positioned that if the target source reflects specularly, the target surface images a viewed subset of the sources into the camera's field of view and images an unviewed subset thereof outside the camera's field of view;
D) employing a field-of-view deflector to move the camera's field of view from a first position, in which at least a first said light source is a member of the viewed subset and at least a second said light source is a member of the unviewed subset, to a second position, in which at least the first light source is a member of the unviewed subset and at least the second light source is a member of the viewed subset;
E) while the field of view is in the first position:
   i) operating the camera to take an image of field of view; and
   ii) while, doing so, keeping each light source of the unviewed subset in the light source's unlit state but causing the first light source to assume the first lights lit state; and
F) while the field of view is in the second position:
   i) operating the camera to take an image of the field of view, and
   ii) while doing so, keeping each light source of the unviewed subset, in the light source's unlit state but causing the second light source to assume the second light lit state.

18. For taking images of a target, a method comprising:
A) providing a camera that has a field of view and is operable to take an image of the field of view and generate output signals representative of the image;
B) providing a target that forms a target surface;
C) providing a lighting system operable to illuminate a target surface selectively from a range of lighting positions such that:

i) if the target source reflects specularly, the target surface images a viewed subset of the lighting positions into the camera's field of view and images an unviewed subset thereof outside the camera's field of view; and
  ii) the memberships of the viewed and unviewed subsets change with changes in the position of the camera's field of view;
D) employing a field-of-view deflector to move the camera's field of view from a first deflector position, in which at least a first said lighting position is a member of the viewed subset and at least a second said lighting position is a member of the unviewed subset, to a second deflector position, in which at least the first lighting position is a member of the unviewed subset and at least the second lighting position is a member of the viewed subset;
E) while the field of view is in the first deflector position:
  i) operating the camera to take an image of field of view; and
  ii) while doing so, preventing the lighting system from illuminating the target surface from the unviewed subset but causing the lighting system to illuminate the target surface from the first lighting position; and
F) while the field of view is in the second deflector position:
  i) operating the camera to take an image of the field of view, and
  ii) while doing so, preventing the lighting system from illuminating the target surface from the unviewed subset but causing the lighting system to illuminate the target surface from the second lighting position.

* * * * *